US008480289B2

(12) United States Patent
Merkhan et al.

(10) Patent No.: US 8,480,289 B2
(45) Date of Patent: Jul. 9, 2013

(54) BONE CEMENT MIXING CARTRIDGE AND METHOD OF USE

(75) Inventors: Imad K. Merkhan, Warsaw, IN (US); H. Gene Hawkins, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 874 days.

(21) Appl. No.: 12/196,394

(22) Filed: Aug. 22, 2008

(65) Prior Publication Data
US 2010/0046315 A1 Feb. 25, 2010

(51) Int. Cl.
*B01F 13/06* (2006.01)

(52) U.S. Cl.
USPC .............................. 366/139; 366/332; 206/222

(58) Field of Classification Search
USPC ............. 366/139, 191, 332; 206/222; 604/87, 604/88
See application file for complete search history.

(56) References Cited

U.S. PATENT DOCUMENTS

| | | | | |
|---|---|---|---|---|
| 1,211,426 | A * | 1/1917 | Farrington | 261/33 |
| 2,527,992 | A * | 10/1950 | Greenberg | 206/220 |
| 2,954,144 | A * | 9/1960 | Elam et al. | 222/82 |
| 3,102,536 | A | 9/1963 | Rose et al. | |
| 3,144,966 | A * | 8/1964 | Cook | 222/136 |
| 4,721,390 | A | 1/1988 | Lidgren et al. | |
| 5,015,101 | A | 5/1991 | Draenert | |
| 5,051,482 | A * | 9/1991 | Tepic | 525/309 |
| 5,108,452 | A | 4/1992 | DeMane et al. | |
| 5,328,262 | A | 7/1994 | Lidgren et al. | |
| 5,370,221 | A | 12/1994 | Magnusson et al. | |
| 5,501,520 | A | 3/1996 | Lidgren et al. | |
| 5,858,020 | A | 1/1999 | Johnson et al. | |
| 5,951,160 | A | 9/1999 | Ronk | |
| 6,155,812 | A | 12/2000 | Smith et al. | |
| 6,286,670 | B1 | 9/2001 | Smith | |
| 6,361,731 | B1 | 3/2002 | Smith et al. | |
| 6,709,149 | B1 * | 3/2004 | Tepic | 366/139 |
| 7,018,089 | B2 * | 3/2006 | Wenz et al. | 366/130 |
| 7,073,936 | B1 * | 7/2006 | Jonsson | 366/139 |
| 7,637,729 | B2 | 12/2009 | Hartman et al. | |

(Continued)

FOREIGN PATENT DOCUMENTS

| | | |
|---|---|---|
| EP | 166724 | 1/1986 |
| EP | 1005900 | 6/2000 |

(Continued)

OTHER PUBLICATIONS

International Search Report and Written Opinion for PCT/US2008/085529 mailed Mar. 17, 2009 claiming priority to U.S. Appl. No. 11/955,601, filed Dec. 13, 2007.

(Continued)

*Primary Examiner* — David Sorkin
(74) *Attorney, Agent, or Firm* — Harness, Dickey

(57) ABSTRACT

A container for bone cement includes a first member defining a chamber, which contains a first ingredient. The chamber also includes a second member movably coupled to the first member. The second member includes a mixing device that is movably disposed within the first chamber, and the second member defines a second chamber containing a second ingredient. The container additional includes an opening device that selectively opens the second chamber and allows the second ingredient to enter from the second chamber into the first chamber. The mixing device is movable within the first chamber to promote mixing of the first ingredient and the second ingredient to prepare the bone cement. A corresponding method of preparing bone cement is also disclosed.

21 Claims, 3 Drawing Sheets

U.S. PATENT DOCUMENTS

| | | | |
|---|---|---|---|
| 2003/0065398 A1 | 4/2003 | Cueille et al. | |
| 2003/0155381 A1 | 8/2003 | Chan | |
| 2005/0004680 A1 | 1/2005 | Saladino et al. | |
| 2005/0027302 A1 | 2/2005 | Cueille et al. | |
| 2005/0143828 A1 | 6/2005 | Collins et al. | |
| 2006/0109737 A1 | 5/2006 | Wilander | |
| 2007/0016215 A1 | 1/2007 | Wilander et al. | |
| 2007/0211563 A1* | 9/2007 | De Vries | 366/139 |
| 2007/0222114 A1 | 9/2007 | Ziran et al. | |
| 2009/0175978 A1 | 7/2009 | Hawkins et al. | |

FOREIGN PATENT DOCUMENTS

| | | |
|---|---|---|
| FR | 2898039 | 9/2007 |
| WO | WO 87/05492 | 9/1987 |
| WO | WO-9851240 | 12/1998 |

OTHER PUBLICATIONS

Biomet Orthopedics, Inc., "The Optivac® Vacuum Mixing System, Intelligent Simplicity," brochure, 2000 (12 pages).

Biomet, "Mixing and Delivery: Optivac®", pp. 1-2, available at http://www.bonecement.com/index.php?id=16933, printed Jul. 15, 2008.

Biomet, "Optivac® Procedure Set," pp. 1-2, available at http://www.bonecement.com/index.php?id=17149, last visited Jul. 15, 2008.

Biomet, Inc., "Optivac® Fusion™ Vacuum Mixing Bowl," pp. 1-2, 2001-2008, available at http://www.biomet.com/hcp/prodpage.cfm?c=0F&p=090505 (printed Feb. 4, 2008).

Biomet, Inc., "Optivac® Vacuum Mixing System," 2001-2008, pp. 1-2, available at http://www.biomet.com/hcp/prodpage.cfm?c=0F&p=0A0403 (printed Feb. 4, 2008).

DePuy Orthopaedics, Inc., "Prostalac Hip Temporary Prosthesis", pp. 1-2, 2001, available at http:/www.fda.gov/cdrh/mda/docs/h000004.html, printed Feb. 8, 2007 (2 pages).

DePuy, "Prostalac® Hip", pp. 1-2, 2005-2006, available at http://www.jnjgateway.com/home.jhtml?page=viewContent&contentId=09008b98800540d1&loc=USENG, printed Feb. 8, 2007 (2 pages).

Exactech, Inc., "InterSpace® Hip," p. 1, available at http://www.exac.com/products/cement-spacers/interspace-hip, last visited Jul. 15, 2008.

Johnson & Johnson, "Prostalac® Hip Essential Product Information," p. 1-3, available at http://www.jnjgateway.com/home.jhtml?contentID=09008b9880054123&loc=USENG&page=viewContent, last visited Jul. 15, 2008.

* cited by examiner

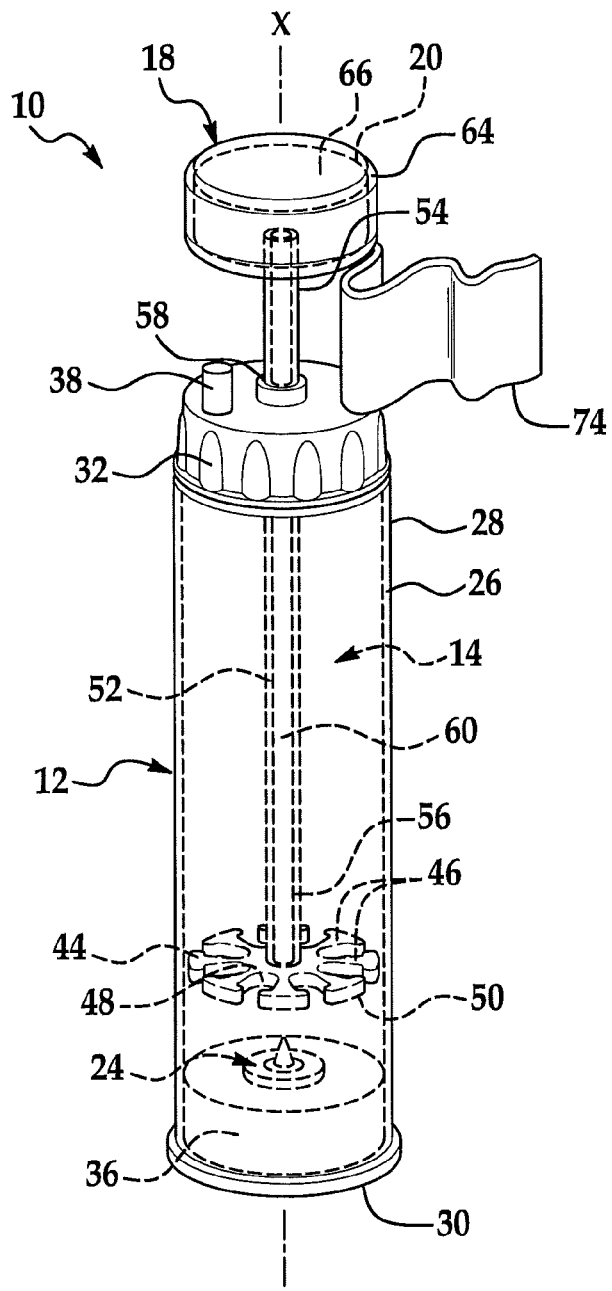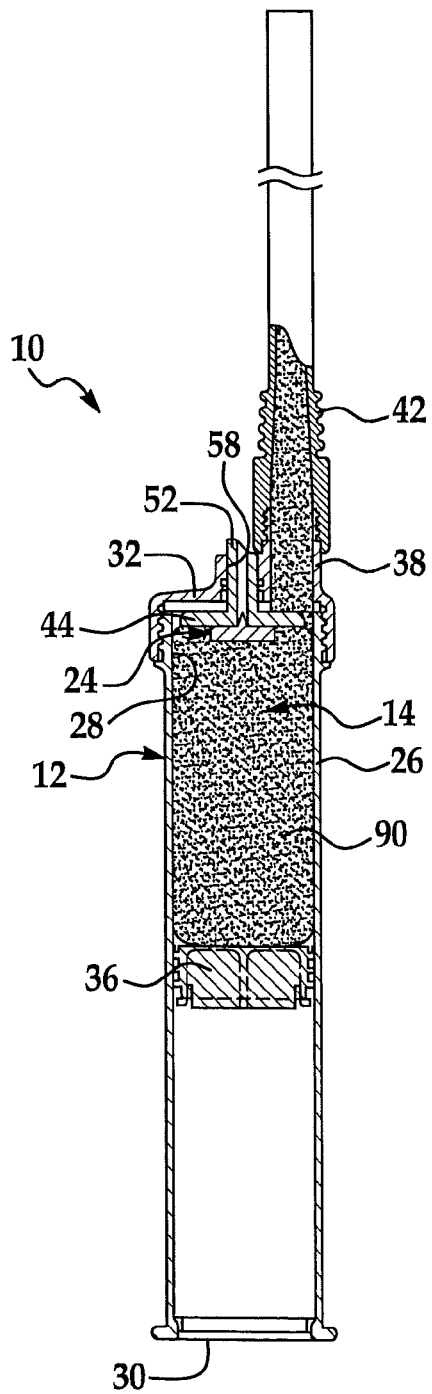
FIG. 1
FIG. 4

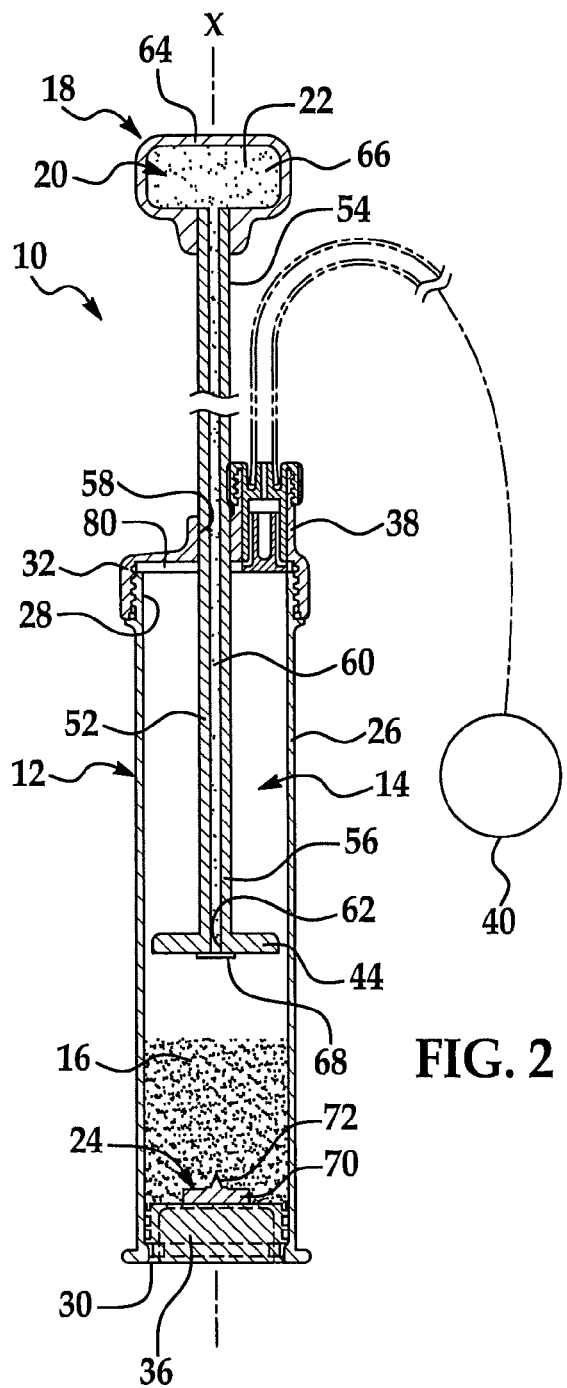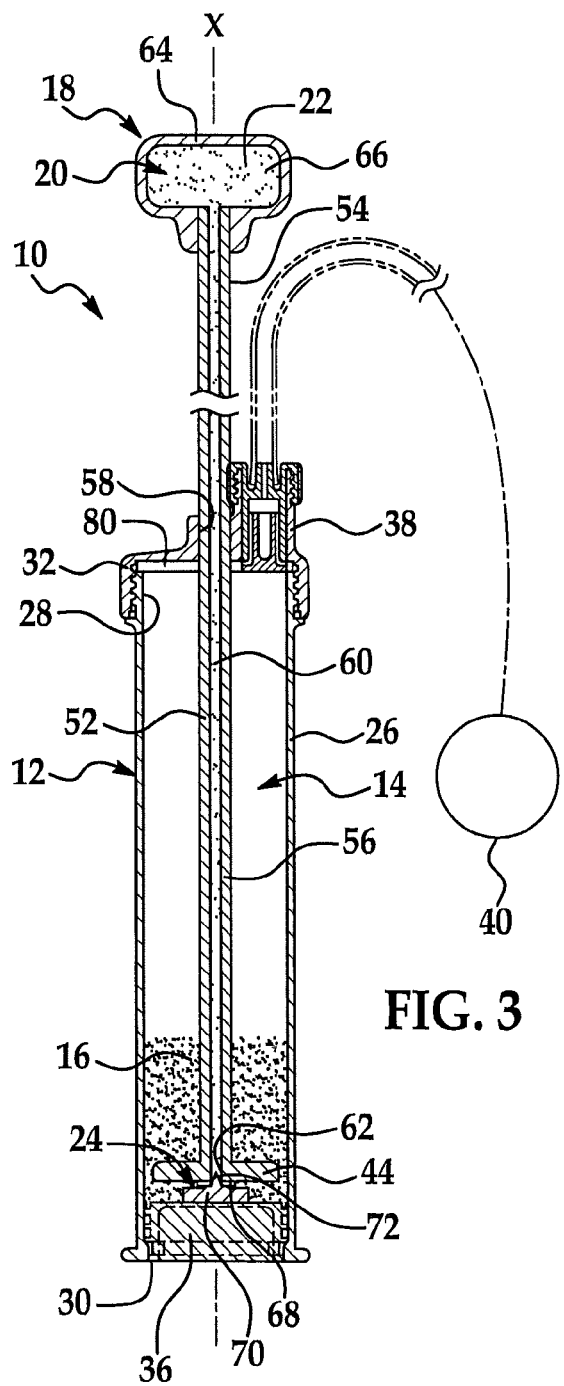

BONE CEMENT MIXING CARTRIDGE AND METHOD OF USE

FIELD

The present disclosure relates to a mixing cartridge and, more particularly, relates to a bone cement mixing cartridge and method of use.

BACKGROUND

The statements in this section merely provide background information related to the present disclosure and may not constitute prior art.

Bone cement is commonly used for bonding implants and prosthetics to bone and for other purposes. Bone cements are often made by mixing multiple ingredients, such as a liquid monomer and a polymeric powder, typically under a vacuum. Once the ingredients are mixed and the bone cement achieves the desired viscosity, the bone cement is delivered to the desired surface (e.g., the bone). Various bone cement mixing and delivery implements have been proposed for facilitating this process.

Although these conventional implements have been adequate for intended uses, they suffer from certain disadvantages. For instance, some containers allow harmful vapors to escape. Furthermore, it can be difficult to ensure proper proportions of the ingredients have been added to the container, and an improper ratio of ingredients can compromise the properties of the bone cement. Additionally, these implements can include a relatively large number of separate components, making them somewhat awkward to use. For instance, ingredients manually decanted from pouches or other containers can cause spills resulting in a messy and potentially dangerous waste of ingredients.

SUMMARY

A container for bone cement is disclosed that includes a first member defining a chamber that is operable to contain a first ingredient. The chamber also includes a second member movably coupled to the first member. The second member includes a mixing device that is movably disposed within the first chamber, and the second member defines a second chamber that is operable to contain a second ingredient. The container additionally includes an opening device that is operable to selectively open the second chamber and allow the second ingredient to enter from the second chamber into the first chamber. The mixing device is movable within the first chamber to promote mixing of the first ingredient and the second ingredient to prepare the bone cement.

In another aspect, a container is disclosed for bone cement. The container includes a first member including a tube with an open first end and an open second end. The first member also includes a cap covering the first end and a piston movably disposed within the tube adjacent the second end. The tube, the cap, and the piston cooperate to define a first chamber. The container further includes a pre-measured first ingredient disposed within the first chamber and a port defined in the cap that enables coupling the first chamber to a vacuum source. Additionally, the container includes a second member movably coupled to the first member. The second member includes a rod, a mixing disc coupled to a first end of the rod, and a handle member that is coupled to a second end of the rod. The second member additionally includes a sealing member. The mixing disc is movably disposed in the first chamber, and the rod movably extends through the cap. The handle member is disposed outside the first chamber, and the first end of the rod includes an aperture that is sealed by the sealing member. The rod and the sealing member cooperate to define at least a portion of a second chamber. The container further includes a pre-measured second ingredient disposed within the second chamber. Also, the container includes a piercing member disposed in the first chamber. The piercing member selectively pierces the sealing member to allow the second ingredient to enter from the second chamber into the first chamber. The handle member is movable relative to the first member to move the mixing disc within the first chamber to promote mixing of the first ingredient and the second ingredient to prepare the bone cement.

A method of producing bone cement in a container is also disclosed. The container includes a first member that defines a first chamber, a second member movably coupled to the first member, and an opening device. The second member includes a mixing device movably disposed within the first chamber. The method includes moving the second member of the container relative to the first member to move the mixing device in the first chamber. The method also includes selectively opening a second chamber defined in the second member with the opening device to cause a second ingredient in the second chamber to enter the first chamber. Also, the method includes mixing the second ingredient with a first ingredient in the first chamber by moving the mixing device in the first chamber.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 1 is a perspective view of a bone cement container according to teachings of the present disclosure;

FIG. 2 is a side view of the bone cement container of FIG. 1 in an initial stage of preparing the bone cement;

FIG. 3 is a side view of the bone cement container of FIG. 1 in an intermediate stage of preparing the bone cement;

FIG. 4 is a side view of the bone cement container of FIG. 1 in a latter stage of preparing the bone cement;

DETAILED DESCRIPTION

Figure 5:
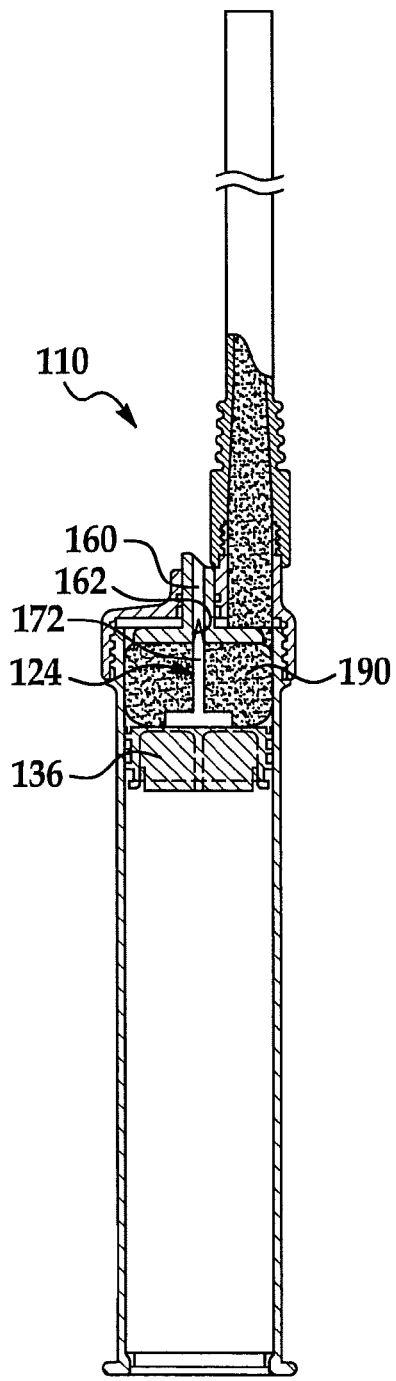
FIG. 5 is a side view of another embodiment of the bone cement container according to the teachings of the present disclosure.

The following description is merely exemplary in nature and is not intended to limit the present disclosure, application, or uses. It should be understood that throughout the drawings, corresponding reference numerals indicate like or corresponding parts and features.

Initially referring to FIG. 1, a container 10 for bone cement is illustrated. It will be appreciated that the container 10 can include one or more features disclosed in U.S. Pat. No. 4,721, 390, filed Oct. 17, 1985, U.S. Pat. No. 5,328,262, filed Feb. 3, 1993, U.S. Pat. No. 5,501,520, filed Apr. 26, 1994, U.S. Patent Publication No. 2006/0109737, filed Apr. 29, 2005, and/or U.S. Patent Publication No. 2007/0016215, filed Aug. 2, 2005, each of which is incorporated by reference in its entirety.

Generally, the container 10 includes a first member 12 which defines a first chamber 14. A first ingredient 16 for the preparation of bone cement is contained within the first chamber 14. The container further includes a second member 18, which is movably coupled to the first member 12. The second member 18 defines a second chamber 20. A second ingredient 22 for the preparation of bone cement is contained within the second chamber 20. Furthermore, the container 10 includes an opening device 24 that selectively opens the second chamber 20 and allows the second ingredient 22 to enter from the second chamber 20 into the first chamber 14. When the first and second ingredients 16, 22 are mixed, bone cement is formed in the first chamber 14. This bone cement can then be dispensed from the first chamber 14 onto any suitable surface (e.g., bone, etc.).

In some embodiments, the first ingredient 16 is a polymeric powder and the second ingredient 22 is a liquid monomer. It will be appreciated that the first and second ingredients 16, 22 can be of any suitable type. For instance, in some embodiments, the first ingredient 16 is ceramic powder. Furthermore, in some embodiments, the second ingredient 22 is an aqueous setting solution. It will also be appreciated that the first ingredient 16 can be contained within the second chamber 20 while the second ingredient 22 can be contained within the first chamber 12.

Furthermore, in some embodiments, the first and second ingredients 16, 22 are pre-measured and provided in the first and second chambers 14, 20, respectively. As such, the container 10 can be packaged and sold so as to be ready for use to make bone cement. Thus, the container 10 provides a convenient and accurate means for making bone cement.

As shown in FIGS. 1-3, the first member 12 can include a tube 26. In some embodiments, the tube 26 is cylindrical so as to define a linear axis X. The tube 26 includes a first open end 28 and a second open end 30 at opposite axial ends of the tube 26. In some embodiments, the first open end 28 is threaded on its outer surface.

The first member 12 can also include a cap 32, which is disposed on and substantially covers the first end 28 of the tube 26. In some embodiments, the cap 32 includes threading on an interior surface for threadably coupling to the first end 28 of the tube 26.

Moreover, the first member 12 can include a piston 36. The piston 36 is movably disposed within the tube 26 to change a volume of the first chamber 14 as will be described in greater below. In an initial state of the container 10 represented in FIG. 1 (i.e., before the first and second ingredients 16, 22 are mixed), the piston 36 is disposed adjacent the second end 30 of the tube 26. The piston 36 moves along the axis X toward the first end 28 once the bone cement is produced as will be described in greater detail below.

The container 10 can also include a port 38. In some embodiments, the port 38 is defined in the cap 32. Also, in some embodiments, the port 38 is threaded on an outer surface. As will be described, the port 38 enables coupling the first chamber 14 to a vacuum source 40 (FIGS. 2 and 3). Furthermore, in some embodiments, the container 10 includes a dispensing tube 42 that removably couples to the port 38 and enables dispensing of the bone cement from the first chamber 14 (FIG. 4).

In some embodiments, the second member 18 is moveable along the axis X relative to the first member 12 to promote mixing of the first and second ingredients 16, 22. Accordingly, in some embodiments, the second member 12 includes a mixing device 44. The mixing device 44 can be flat and disc-shaped with a plurality of legs 46 that extend transversely from the axis X. The legs 46 are disposed in spaced relationship relative to each other so as to define a space 48 between each of the legs 46. Furthermore, each leg 46 includes an enlarged head 50 at a terminal end thereof. The mixing device 44 is movably disposed in the first chamber 14. More specifically, in some embodiments, the mixing device 44 is moveable along the axis X toward the first and second ends, 28, 30 of the tube 26. Also, in some embodiments, the legs 46 are long enough to substantially span the width of the tube 26.

The second member 18 can also include an extension member 52. In some embodiments, the extension member 52 is elongate and rod-shaped. The extension member 52 includes a first end 54 and a second end 56 that is fixedly coupled to the mixing device 44. The extension member 52 movably extends through a central aperture 58 in the cap 32 so as to be substantially aligned with the axis X. As such, the first end 54 of the extension member 52 extends out of the first chamber 14.

The extension member 52 defines a passage 60 therein. The passage 60 partially defines the second chamber 20. Furthermore, the extension member 52 includes an aperture 62 (FIGS. 2 and 3) at the second end 56 of the extension member 52. As will be described in greater detail, the second ingredient 22 flows from the second chamber 20 into the first chamber 14 through the aperture 62.

The second member 18 can also include a handle member 64. In some embodiments, the handle member 64 is disc-shaped and is centered about the axis X. The handle member 64 is fixedly coupled to the first end 54 of the extension member 52. As such, the handle member 64 is disposed outside the first chamber 14 of the container 10.

In some embodiments, the handle member 64 is substantially hollow so as to define a handle chamber 66 therein. The handle chamber 66 partially defines the second chamber 20. The handle chamber 66 is in communication (e.g., fluid communication) with the passage 60 of the extension member 52. As will be described, the handle member 64 and the extension member 52 are moveable relative to the first member 12 to move the mixing device 44 within the first chamber 14 to promote mixing of the first ingredient and the second ingredient, 16, 22 and to prepare the bone cement.

Furthermore, the second member 18 can include a sealing member 68 (FIGS. 2 and 3). In some embodiments, the sealing member 68 is a thin membrane that seals the aperture 62 of the extension member 52. It will be appreciated that the sealing member can be made of any suitable material, such as aluminum foil coated with polyethylene.

Thus, the handle chamber 64 and the passage 60 collectively define the second chamber 20. In other words, the handle member 64, the extension member 52, and the sealing member 68 cooperate to define the volume of the second chamber 20. Likewise, the tube 26, the cap 32, and the piston 36 cooperate to define the volume of the first chamber 14. It will be appreciated that the first ingredient 16 remains independent of the second ingredient 22 until the sealing member 68 unseals the aperture 62 of the extension member 52.

Additionally, the opening device 24 can include a base 70 and a piercing member 72. In some embodiments, the base 70 is disc-shaped, and the piercing member 72 comes to a sharpened point. The opening device 24 is disposed within the first chamber 14 between the piston 36 and the mixing device 44. In some embodiments, the opening device 24 is supported on the piston 36 such that the sharpened point of the piercing member 72 faces the sealing member 68. Furthermore, in some embodiments, the passage 60, the sealing member 68, and the piercing member 72 are substantially aligned along the axis X. Moreover, in some embodiments, the width of the base 70 is substantially less than the width of the first chamber 14. As will be described, the opening device 24 selectively opens the second chamber 20 by piercing the sealing member 68, thereby selectively unsealing the aperture 62 of the extension member 52.

Moreover, the container 10 can also include a guard member 74 (FIG. 1). Generally, the guard member 74 selectively limits movement of the handle member 64, the extension member 52, and the mixing device 44 toward the opening device 24. As such, the guard member 74 reduces the likelihood of inadvertent piercing of the sealing member 68 by the piercing member 72 of the opening device 24. In some embodiments, the guard member 74 includes a relatively thin, flexible strip of material or membrane that is wrapped around the container 10 and disposed between the handle member 64 and the cap 32. In other embodiments, the guard member 74 includes one or more removable rods that extend between the handle member 64 and the cap 32. Furthermore, in some embodiments, the guard member 74 is removably coupled to the handle member 64 and/or the cap 32. The guard member 74 can be integral, molded, glued, snap-fit, welded or otherwise removably coupled to the handle member 64 and the cap 32. Additionally, in some embodiments, the guard member 74 seals the space between the handle member 64 and the cap 32 such that the port 38 is substantially sealed from contamination. Also, the guard member 74 can be disposed anywhere on the container 10, including inside the first chamber 14.

Thus, in order to make and produce bone cement using the pre-packaged container 10 represented in FIG. 1, the guard member 74 is first removed from the handle member 64 and the cap 32. This exposes the port 38 and allows movement of the second member 18 relative to the first member 12.

Then, the vacuum source 40 is operatively coupled to the first chamber 14 via the port 38. In some embodiments, a filter device 80 is disposed adjacent the first end 28 and at least partially over the port 38 for inhibiting bone cement and/or the first or second ingredients 16, 22 from being sucked into the vacuum source 40.

Next, the user grasps the handle member 64 and pushes the handle member 64 downward along the axis X such that the mixing device 44 and the sealing member 68 move toward the piercing member 72 (FIG. 2). Eventually, the piercing member 72 pierces through the sealing member 68 and unseals the aperture 62. Because of the vacuum provided by the vacuum source 40, the second ingredient 22 flows from the handle chamber 66 and the passage 60 through the aperture 62 and into the first chamber 14 to mix with the first ingredient 16. In some embodiments, once the sealing member 68 is pierced, the second ingredient 22 flows out of small openings pierced in the sealing member 68, and these openings are sufficiently small to inhibit backflow from the first chamber 14 to the passage 60. Also, in some embodiments, the piercing member 72 substantially plugs the aperture 62 once the second ingredient 22 flows out into the first chamber 14 to inhibit backflow from the first chamber 14 into the passage 60. In still further embodiments, the passage 60 includes a one way valve that allows the second ingredient 22 to flow into the first chamber 14 but that inhibits backflow from the first chamber 14 into the passage 60.

Once the second ingredient 22 begins flowing into the first chamber 14, the user can agitate the mixture of the first and second ingredients 16, 22 by grasping the handle member 64 and moving the mixing device 44 up and down along the axis X and/or rotating the mixing device 44 about the axis X. The legs 46 and the heads 50 of the mixing device 44 facilitate mixing of the first and second ingredients 16, 22. In some embodiments, once the first and second ingredients 16, 22 are mixed, a reaction occurs to form the bone cement 90 (FIG. 4).

Once the first and second ingredients 16, 22 are sufficiently mixed (e.g., into a homogeneous mixture) the user grasps the handle member 64 and moves the handle member 64, the extension member 52, and the mixing device 44 upward along the axis X toward the first end 28 of the tube 26. In some embodiments, the opening device 24 is detachably supported by the piston 36 such that the opening device 24 remains frictionally attached to the second member 18 once the piercing member 72 pierces the sealing member 68, and movement of the second member 18 toward the first end 28 of the tube 26 pulls the opening device 24 toward the first end 28 of the tube 26 (FIG. 4).

Continued operation of the vacuum source 40 draws the piston 36 upward along the axis X toward the first end 28 of the tube 26 and also draws out air bubbles within the bone cement 90. It will be appreciated that this movement of the piston 36 substantially eliminates open space between the piston 36 and the cap 32 and substantially gathers the bone cement 90 therebetween. In some embodiments, the piston 36 moves selectively away from the second end 30. For instance, the piston 36 and the tube 26 can include corresponding locking tabs. The locking tabs retain the piston 36 in position adjacent the second end 30. Then, when the user so chooses, the piston 36 can turn the piston 36 about the axis X to unlock the corresponding locking tabs and allow the piston 36 to move toward the first end 28 of the tube 26.

Then, once the vacuum 40 is removed, the extension member 52 can be broken just above the cap 32, and the filter device 80 can be removed from the port 38. Subsequently, the dispensing tube 42 can be threaded to the port 38, and the container 10 can be loaded into a dispensing device, such as a bone cementing gun (not specifically shown) for dispensing the bone cement 90 to the intended area. It will be appreciated that the opening device 24 substantially seals the passage 60 such that the bone cement 90 is unlikely to flow out of the first chamber 14 through the passage 60. It will also be appreciated that the width of the base 70 is such that the bone cement 90 is able to bypass the base 70 and flow out of the first chamber 14 through the port 38.

Referring now to FIG. 5, a container 110 is illustrated according to various other embodiments of the present disclosure. Features that are similar to those of the container 10 of FIGS. 1-4 are identified with similar reference numerals increased by 100.

As shown in FIG. 5, the container 110 includes an opening device 124 wherein the piercing member 172 remains attached to the piston 136. As shown, the piercing member 172 has a length sufficient enough to extend from the piston 136 and into the aperture 162 to substantially plug the aperture 162. For example, the length of the piercing member 172 is approximately two centimeters in some embodiments. Because the piercing member 172 substantially plugs the aperture 162, the bone cement 190 is unlikely to backflow into the passage 160. Also, the bone cement 190 is less likely to be contaminated.

Figure 6:
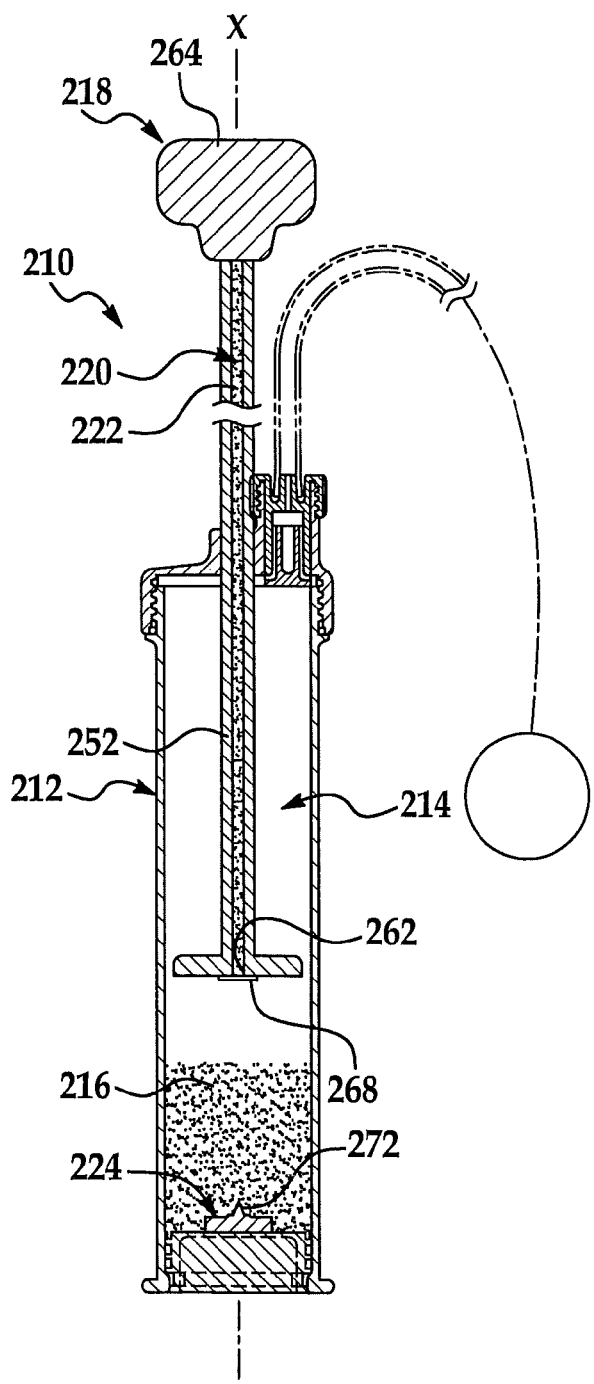
FIG. 6 is a side view of another embodiment of the bone cement container according to the teachings of the present disclosure.

Referring now to FIG. 6, a container 210 is illustrated according to various other embodiments of the present disclosure. Features that are similar to those of the container 10 of FIG. 1-4 are identified with similar reference numerals increased by 200.

As shown in FIG. 6, the container 210 includes a first member 212 and a second member 218. The second member 218 includes a handle member 264 and an extension member 252. The second chamber 220 is defined substantially within only the extension member 252. It will be appreciated that the extension member 252 can be of any suitable width, diameter, length, or other dimension so as to encapsulate a predetermined amount of the second ingredient 222.

By depressing the handle member 264 and moving the extension member 252 toward the opening device 224, the piercing member 272 pierces the sealing member 268. This unseals the aperture 262 in the extension member 252, thereby allowing the second ingredient 222 to flow out from the second chamber 220 and into the first chamber 214 to mix with the first ingredient 216. It will be appreciated that the container 210 can be simpler to manufacture because the second chamber 220 is defined substantially within only the extension member 252.

In summary, the container 10 allows for convenient manufacture of bone cement 90 because the first and second ingredients 16, 22 can be pre-measured and disposed within the first and second chambers 14, 20, respectively and because mixing the ingredients 16, 22 can be performed with relatively few steps. Also, the first and second ingredients 16, 22 can be mixed substantially without exposing the user to harmful vapors because the mixing can be performed under vacuum. Moreover, the sterility of the ingredients 16, 22 and ultimately the bone cement 90 can be ensured using the container 10. Furthermore, the container 10 is relatively compact for additional convenience.

Moreover, the foregoing discussion discloses and describes merely exemplary embodiments of the present disclosure. One skilled in the art will readily recognize from such discussion, and from the accompanying drawings and claims, that various changes, modifications and variations may be made therein without departing from the spirit and scope of the disclosure as defined in the following claims.

What is claimed is:

1. A container for bone cement, the container comprising:
   a first member defining a first chamber operable to contain a first ingredient;
   a second member movably coupled to the first member, the second member including a closed handle member and extension member, the second member further including a mixing device that is movably disposed within the first chamber, the second member defining a second chamber operable to contain a second ingredient;
   an opening device disposed within the first chamber and operable for selectively opening the second chamber and allowing the second ingredient to enter from the second chamber into the first chamber, the mixing device being movable relative to the opening device and movable within the first chamber to promote mixing of the first ingredient and the second ingredient to prepare the bone cement; and
   a port defined in the first member, the port operable for providing suction to the first chamber to suck the second ingredient from the second chamber into the first chamber.

2. The container of claim 1, wherein the extension member includes a passage defined therein and the second member further includes a sealing member that seals an aperture of the extension member, the passage at least partially defining the second chamber, and the opening device selectively unsealing the aperture to allow the second ingredient to enter from the passage into the first chamber.

3. The container of claim 2, wherein the opening device selectively pierces the sealing member to selectively unseal the aperture.

4. The container of claim 3, wherein the opening device includes a piercing member that selectively pierces the sealing member and that substantially plugs the aperture to inhibit backflow from the first chamber into the passage.

5. The container of claim 4, wherein the first member includes a tube and a piston movably disposed within the tube, wherein the opening device is detachably supported by the piston, the opening device detaching from the piston to substantially plug the aperture.

6. The container of claim 4, wherein the first member includes a tube and a piston movably disposed within the tube, wherein the opening device is supported by the piston, and wherein the opening device has a length sufficient enough to extend from the piston and substantially plug the aperture.

7. The container of claim 2, wherein the handle member has a handle chamber defined therein, the handle chamber at least partially defining the second chamber and in communication with the passage, the handle member disposed outside the first chamber.

8. The container of claim 7, wherein the extension member includes a first end that is coupled to the handle member and a second end that is coupled to the mixing device, the handle member being movable relative to the first member to move the mixing device within the first chamber to promote mixing of the first ingredient and the second ingredient to prepare the bone cement.

9. The container of claim 8, further comprising a cap disposed on a first end of the first member, the extension member movably extending through the cap.

10. The container of claim 9, wherein the cap defines the port, the port operable to removably couple to a vacuum source for providing suction to the first chamber.

11. The container of claim 10, further comprising a dispensing tube that removably couples to the port and that enables dispensing of the bone cement from the first chamber.

12. The container of claim 2, further comprising a guard member that selectively limits movement of the sealing member toward the opening device.

13. The container of claim 12, wherein the guard member is disposed between the first member and the second member, and wherein the guard member is removably coupled to at least one of the first member and the second member.

14. The container of claim 1, wherein the first member includes a tube and a piston movably disposed within the tube, the piston movable to change a volume of the first chamber.

15. The container of claim 1, wherein the mixing device includes a plurality of legs that are disposed at a distance from each other.

16. The container of claim 1, wherein the first chamber contains the first ingredient and the first ingredient comprises a ceramic powder.

17. The container of claim 1, wherein the second chamber contains the second ingredient and the second ingredient comprises an aqueous setting solution.

18. The container of claim 1, wherein the second member further includes a handle member and an extension member, and wherein the second chamber is defined in at least one of the handle member and the extension member.

19. A container for bone cement comprising:
   a first member including a tube with an open first end and an open second end, a cap covering the first end, and a piston movably disposed within the tube adjacent the second end, the tube, the cap, and the piston cooperating to define a first chamber;
   a pre-measured first ingredient disposed within the first chamber;

a port defined in the cap of the first member, the port operable for coupling the first chamber to a vacuum source to provide suction to the first chamber;

a second member movably coupled to the first member, the second member including a rod, a mixing disc coupled to a first end of the rod, a handle member that is closed and coupled to a second end of the rod, and a sealing member, the mixing disc movably disposed in the first chamber, the rod movably extending through the cap, the handle member disposed outside the first chamber, the first end of the rod including an aperture that is sealed by the sealing member, the handle member, the rod and the sealing member cooperating to define a second chamber;

a pre-measured second ingredient disposed within the second chamber; and a piercing member disposed in the first chamber, the mixing disc being movable relative to the piercing member, the piercing member operable to selectively pierce the sealing member, whereupon the suction from the vacuum source sucks the second ingredient from the second chamber into the first chamber, the handle member being movable relative to the first member to move the mixing disc within the first chamber to promote mixing of the first ingredient and the second ingredient to prepare the bone cement.

20. The container of claim 1, wherein the port has a threaded outer surface.

21. The container of claim 1, further comprising a filter device that is disposed at least partially over the port for inhibiting at least one of the first and second ingredients from being sucked into the vacuum source.

* * * * *

UNITED STATES PATENT AND TRADEMARK OFFICE
CERTIFICATE OF CORRECTION

| | | |
|---|---|---|
| PATENT NO. | : 8,480,289 B2 | Page 1 of 1 |
| APPLICATION NO. | : 12/196394 | |
| DATED | : July 9, 2013 | |
| INVENTOR(S) | : Merkhan et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 998 days.

Signed and Sealed this
Twenty-seventh Day of January, 2015

Michelle K. Lee
*Deputy Director of the United States Patent and Trademark Office*